(12) United States Patent
Niwa et al.

(10) Patent No.: US 7,255,310 B2
(45) Date of Patent: Aug. 14, 2007

(54) HOLDER FOR A MEDICAL DEVICE (75) Inventors: Hiroshi Niwa, Koganei (JP); Fumiyuki Onoda, Tama (JP); Michio Sato, Hachioji (JP); Akira Taniguchi, Hachioji (JP)

(73) Assignee: Olympus Corporation, Tokyo (JP)

( * ) Notice: Subject to any disclaimer, the term of this patent is extended or adjusted under 35 U.S.C. 154(b) by 76 days.

(21) Appl. No.: 10/544,263

(22) PCT Filed: Aug. 22, 2003

(86) PCT No.: PCT/JP03/10616

§ 371 (c)(1),
(2), (4) Date: Aug. 2, 2005

(87) PCT Pub. No.: WO2005/018438

PCT Pub. Date: Mar. 3, 2005

(65) Prior Publication Data
US 2006/0169851 A1    Aug. 3, 2006

(51) Int. Cl.
*A62C 13/76* (2006.01)
(52) U.S. Cl. ............... 248/75; 248/51; 600/102
(58) Field of Classification Search ........... 248/75, 248/79, 80; 604/178; 600/102
See application file for complete search history.

(56) References Cited
U.S. PATENT DOCUMENTS 4,998,692 A * 3/1991 Shigeki et al. ............. 248/56
5,005,790 A * 4/1991 Harris, III ................. 248/75
5,415,287 A   5/1995 Hamano et al.
5,806,822 A   9/1998 Schulz
6,077,074 A   6/2000 Homra
6,352,503 B1  3/2002 Matsui et al.
2002/0143235 A1 10/2002 Pagliuca
2003/0120216 A1  6/2003 Bouphavichith et al.

FOREIGN PATENT DOCUMENTS

JP    2001-239754    8/2001
JP    2003-245249    9/2003

* cited by examiner

*Primary Examiner*—Ramon O Ramirez
(74) *Attorney, Agent, or Firm*—Scully, Scott, Murphy & Presser, P.C.

(57) ABSTRACT

A holding device 20 includes a fixed portion 21 having a rectangular hole 21a and locking grooves 21b; a holding groove 22 having a notch portion 22a through which an intermediated portion of a probe 1 passes; and a holding hole 23 through which the distal portion of the probe 1 is inserted. The depth of the holding groove 22 is formed to a sufficient extent to allow the intermediate portion 1b to be pressed down into the holding groove at least twice in a superimposed state. The width of the notch portion 22a is formed so as to prevent the intermediated portion 1b from falling out. In order to locate the top portion 23a of the holding hole 23 on the lower side than the bottom portion 22c of the holding groove 22, a spacing B is provided therebetween. A rectangular projection 31a is engaged in a rectangular hole 21a in the fixed portion 21.

4 Claims, 7 Drawing Sheets

HOLDER FOR A MEDICAL DEVICE

TECHNICAL FIELD

The present invention relates to a holding device in which an elongated therapeutic device or probe to be inserted through a therapeutic device insertion channel of an endoscope, is to be placed.

BACKGROUND ART

In recent years, endoscopes are in widespread use in medical field and industrial field. In particular, the endoscope having a soft insertion portion allows an organ in a body cavity in the depths to be diagnosed without being incised, by inserting the insertion portion of the endoscope into the bending body cavity. Also, as necessary, inserting a therapeutic device through a therapeutic device insertion channel provided in the endoscope, enables a treatment/therapy such as collection of a tissue biopsy or removal of a polyp.

However, for example, when examining a lower digestive tract by inserting an endoscope having an elongated insertion portion into the body cavity from the anus side, a measure of skill has been required in order to smoothly insert the insertion portion into the winding digestive tract. This is because it cannot be perceived where the distal end of the insertion portion is located in the body cavity, or how is a current inserted state of the insertion portion.

In order to detect an inserted state of the insertion portion of the endoscope, Japanese Patent Application No. 2001-239754, to the same assignee as this application, proposes an insertion shape detecting probe. This insertion shape detecting probe can detect an insertion shape with a high degree of accuracy, by inserting it into a therapeutic device insertion channel provided in the endoscope, as necessary.

However, besides this insertion shape detecting probe, therapeutic devices or the like are also inserted into the therapeutic insertion channel. Therefore, when attempting to insert a therapeutic device into the therapeutic insertion channel, it is necessary to once withdraw the insertion shape detecting probe from the therapeutic insertion channel, and to suspend it from a holding device or the like while using another therapeutic device.

However, since the insertion shape detecting probe has an elongated shape, it has been difficult to suspend the insertion shape detecting probe without allowing it to contact a floor of an examination room or the like. Hence, it has been extremely difficult for a single operator to perform this work.

Accordingly, it is an object of the present invention to provide a holding device allowing a single operator to easily perform suspending work for a holding device such as the insertion shape detecting probe.

DISCLOSURE OF INVENTION

The present invention includes a fixed portion that is removable with respect to a predetermined member; a holding groove formed further toward the front side than the fixed portion and having a notch portion with a predetermined width, the notch portion being passed through by an intermediate portion of the therapeutic device or probe; and a holding hole into which the distal portion of the therapeutic device or probe is placed, the holding hole having a predetermined diameter and being formed further toward the front side than the holding groove. With these arrangements, the intermediate portion of the therapeutic device or probe is placed into the holding groove through the notch portion, and lastly, the distal portion of the therapeutic device or probe is inserted through the holding hole, whereby the elongated therapeutic device or probe can be stably suspended from the holding device in a loop shape.

Also, in the present invention, the depth of the holding groove is formed to a sufficient extent to allow the intermediate portion of the therapeutic device or probe to be pressed down into the holding groove at least twice. With this feature, the intermediate portion of the therapeutic device or probe is placed in the holding groove a plurality of times via the notch portion, thus forming a plurality of loops.

Furthermore, in the present invention, a predetermined spacing is provided between the bottom portion of the holding groove and the top portion of the holding hole. By virtue of this feature, when the distal portion of the therapeutic device or probe that forms loops is lastly inserted through the holding hole, or when the probe suspended from the holding device is again inserted through a therapeutic device insertion channel, it is possible to hold the distal portion of the probe without allowing a hand to contact the intermediate portion of the probe.

BEST MODE FOR CARRYING OUT THE INVENTION

To explain the present invention in more detail, descriptions will be given below with reference to the accompanying drawings.

Figure 1:
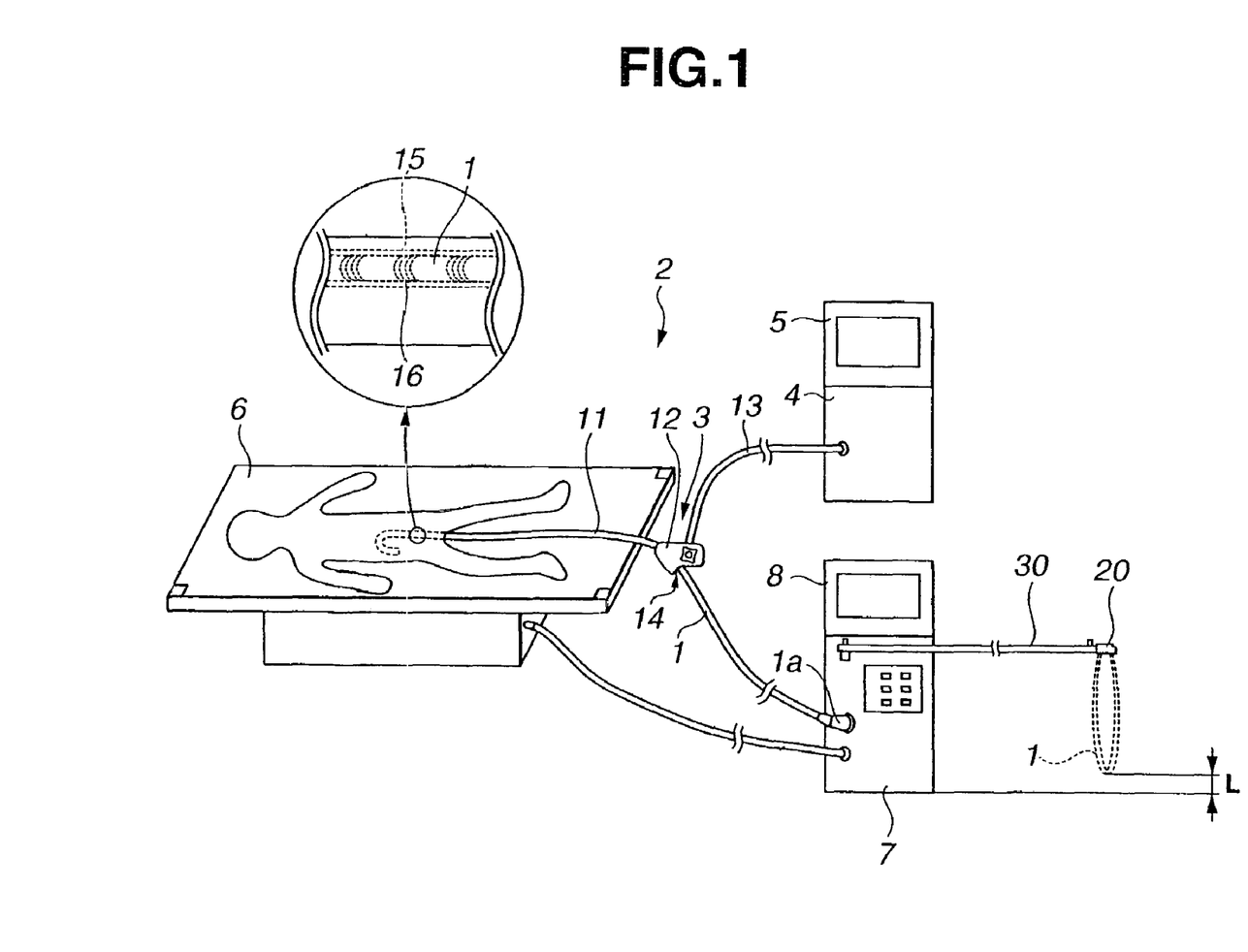
FIG. 1 is a block diagram illustrating an insertion portion shape observation device.

As shown in FIG. 1, a holding device 20 according to the present invention is used in an endoscope apparatus 2 in which, for example, an insertion shape detecting probe (hereinafter abbreviated to a "probe") 1 is employed.

The endoscope apparatus 2 comprises an endoscope 3, a video processor 4, a first monitor 5, a bed 6 for insertion shape detection, an insertion shape detecting device 7, a second monitor 8, and an arm member 30.

The endoscope 3 is inserted into a body cavity or the like of a subject, for example, through the anus thereof, for observation of an area to be observed. The video processor 4 produces image signals from image-pickup signals obtained by picking up an image with the endoscope 3. The first monitor 5 displays the image signals from the video processor 4 as an endoscope image. The subject lies on the bed 6 for insertion shape detection (hereinafter abbreviated to the "bed"). The bed 6 detects magnetic fields from the probe 1 inserted in the subject. The insertion shape detecting device 7 drives the probe 1, and also outputs image signals obtained by imaging an insertion shape of the endoscope 3 in the body cavity, based on signals corresponding to the magnetic fields detected by the bed 6. The second monitor 8 displays an insertion portion shape image based on the image signals outputted from the insertion shape detecting device 7. The arm member 30 is an elongated fixture, and the proximal portion thereof is fitted to the insertion shape detecting device 7, for example, so as to be turnable. The holding device 20 is fitted to a mounting portion, which is the distal portion of the arm member 30.

The endoscope 3 is configured to comprise an insertion portion 11, operation portion 12, and universal cord 13. The insertion portion 11 has an elongated shape, and is inserted into a body cavity. The operation portion 12 is juxtaposed with the proximal portion of the insertion portion 11, and also serves as a grasping portion. The universal cord 13 extends from a side portion of the operation portion 12, and is connected to an external unit such as the video processor 4.

The probe 1 is inserted into the therapeutic device insertion channel 15 through a therapeutic device insertion port 14. As shape detecting elements, the probe 1 has, for example, a plurality of source coils 16 that are each magnetic field generating elements for generating a magnetic field. The probe 1 is connected to the insertion shape detecting device 7 through a connector portion 1a.

During operation, the arm member 30 is turnably disposed at an ease-to-use place, for example, on the bed 6 side, on the insertion shape detecting device 7, on a trolley (not shown) on which the video processor 4 is to be mounted, or the like. Thereby, the holding device can be disposed close at an operator's hand. As indicated by the broken lines in FIG. 1, the probe 1 is placed in the holding device 20, so that an intermediate portion and the distal portion of the elongated probe 1 is suspended therefrom without contacting a floor surface.

Figure 2:
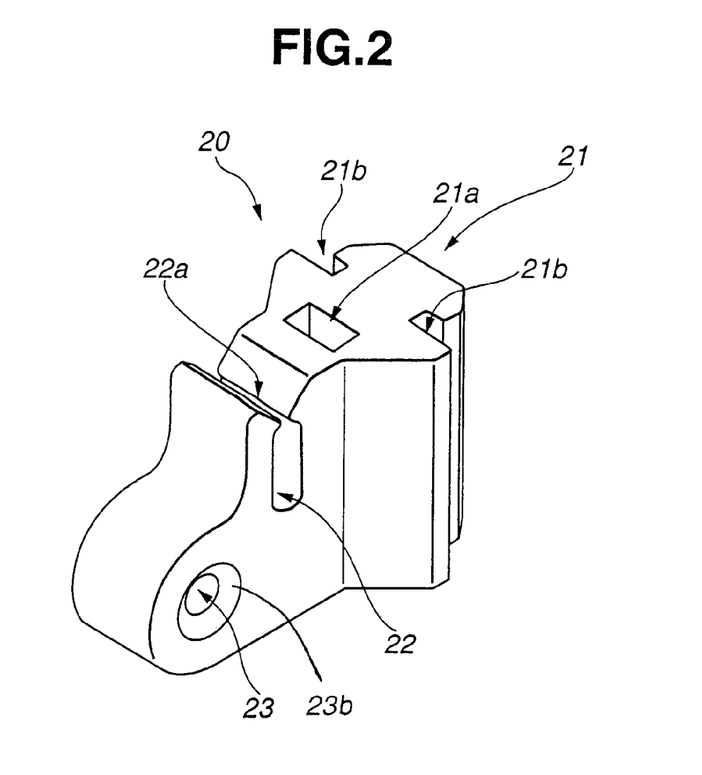
FIG. 2 is a perspective view of a holding device.
Figure 3:
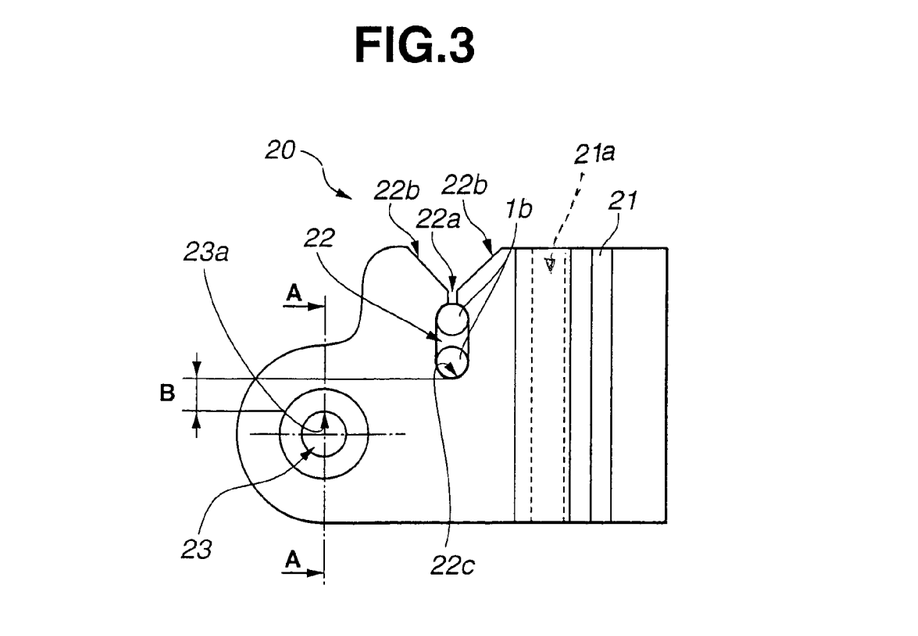
FIG. 3 is a side view of the holding device.
Figure 4:
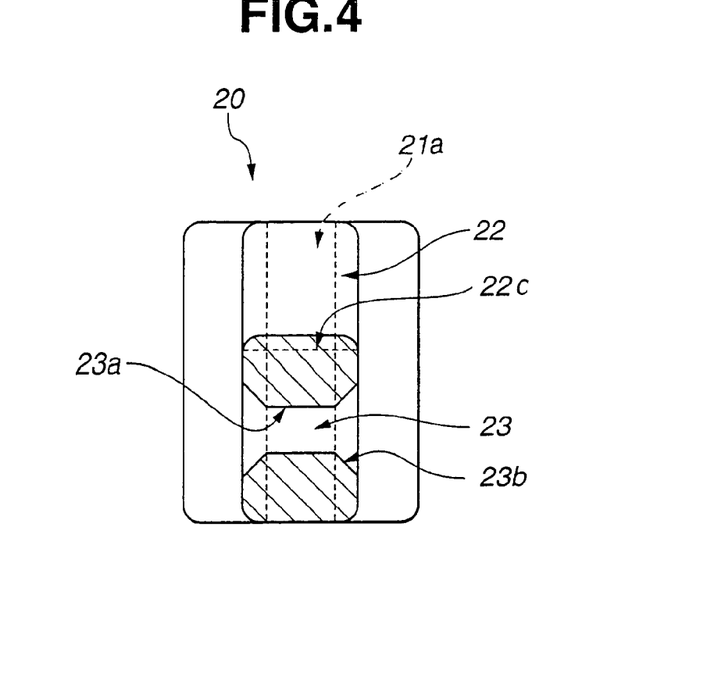
FIG. 4 is a sectional view taken along the line A-A in FIG. 3.

More specific descriptions of the holding device 20 are now made with reference to FIGS. 2 to 4.

When intended for holding the probe 1, the holding device 20 is formed of an elastic material, such as silicon rubber. The objective is to prevent the outer surface of the probe 1 from being scratched, and to prevent the occurrence of a malfunction caused by giving a shock or the like to the source coils 16 provided in the probe 1 when placing the intermediate portion of the probe 1 into the holding device 20.

As shown in FIG. 2, the holding device 20 comprises a fixed portion 21, a holding groove 22 formed further toward the front side than the fixed portion 21, and a holding hole 23 formed further toward the front side than the holding groove 22. The fixed portion 21 includes a rectangular hole 21a and a pair of locking grooves 21b that are removably disposed with respect to the mounting portion (described later) that is provided at the distal portion of the arm member 30. The holding groove 22 has a notch portion 22a having a predetermined width, the notch portion being passed through by the intermediate portion of the probe 1. The diameter of the holding hole 23 is formed so that the distal portion of the probe 1 is inserted therethrough.

As shown in FIG. 3, the depth of the holding groove 22 is formed to a sufficient extent to allow the intermediate portion 1b of the probe 1 to be pressed down into the holding groove 22 and to be placed at least twice in a superimposed state with free play. The width of the notch portion 22a is formed smaller than the diameter of the intermediate portion 1b. The objective is to prevent the intermediate portion 1b of the probe 1 placed in the holding device 20 from falling out.

Therefore, when the intermediate portion 1b is to be placed into the holding groove 22, the intermediate portion 1b pushes the notch portion 22a open against the elastic force of the notch portion 22a, whereby the intermediate portion 1b is passed through the holding groove 22.

Here, reference numeral 22b denotes an inclined surface for guiding the intermediate portion 1b to the notch portion 22a. Providing the inclined surface 22b allows the intermediate portion 1b to be smoothly guided to the notch portion 22a and to be placed into the holding groove 22.

In order that the top portion 23a of the holding hole 23 is located lower than the bottom portion 22c of the holding groove 22, a predetermined spacing B is provided therebetween, as shown in FIGS. 3 and 4. Thereby, when the distal portion 1c of the probe 1 is inserted into the holding hole 23, or when the distal portion 1c of the probe 1 is withdrawn from the holding hole 23, it is possible to prevent a hand from contacting the intermediate portion 1b of the probe 1 placed in the holding groove 22.

Reference numeral 23b denotes a guide surface formed as an inclined surface for smoothly guiding the distal end 1d of the probe 1 to the holding hole 23, and is formed on either of the opposite sides of the holding hole 23. Providing the guide surfaces 23b allows the distal portion 1c of the probe 1 to be smoothly guided to the holding hole 23.

Figure 5:
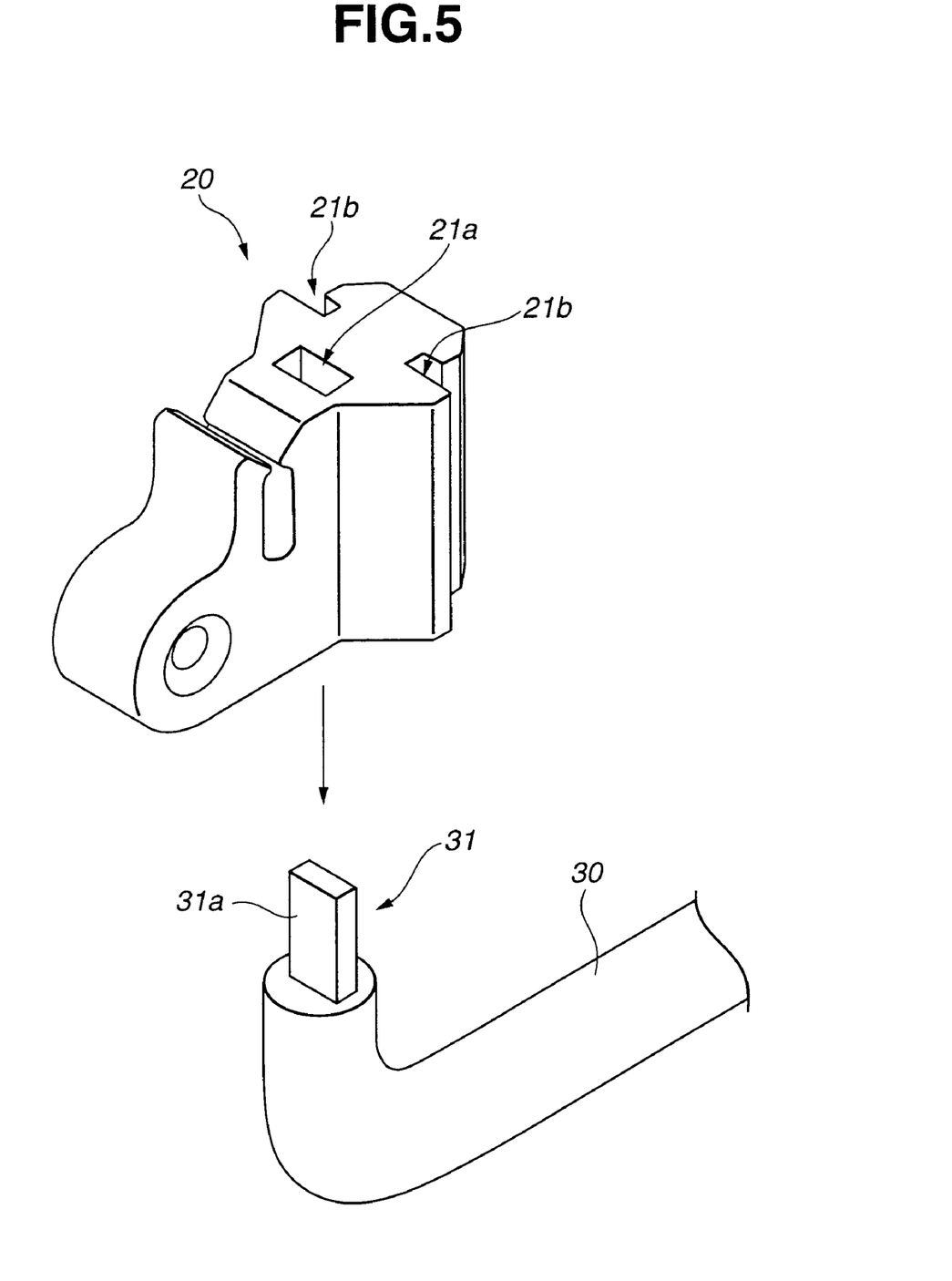
FIG. 5 is a diagram illustrating the relationship between the holding device and a fixture.

As shown in FIG. 5, a rectangular projection 31a constituting a mounting portion 31 formed at the distal portion of the arm member 30, is engaged into a rectangular hole 21a in the fixed portion 21. The size of the rectangular hole 21a is made a little smaller than the external size of the rectangular projection 31a. Therefore, the rectangular hole 21a is reliably fitted to the rectangular projection 31a under the elastic force of the holding device 20.

Figure 6:
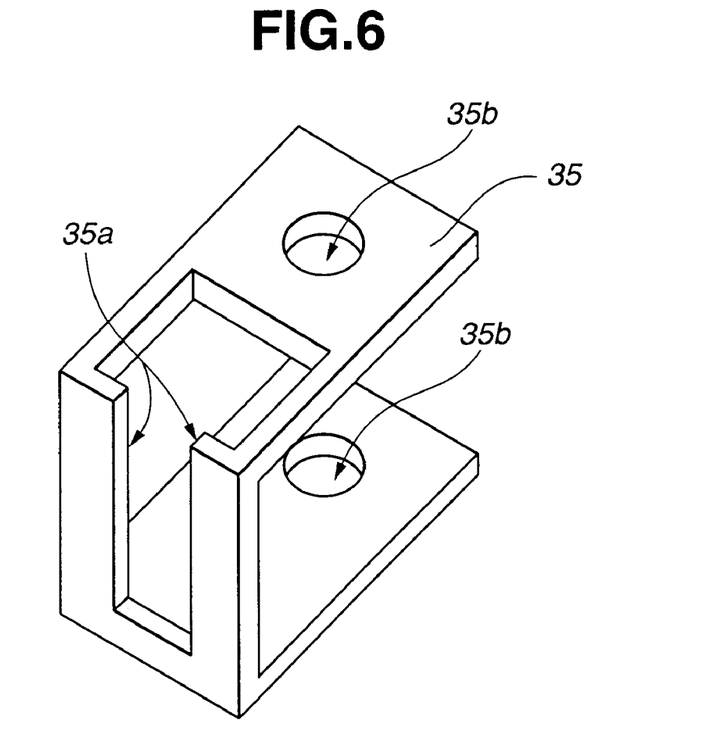
FIG. 6 is a perspective view of a fixture having another construction.
Figure 7:
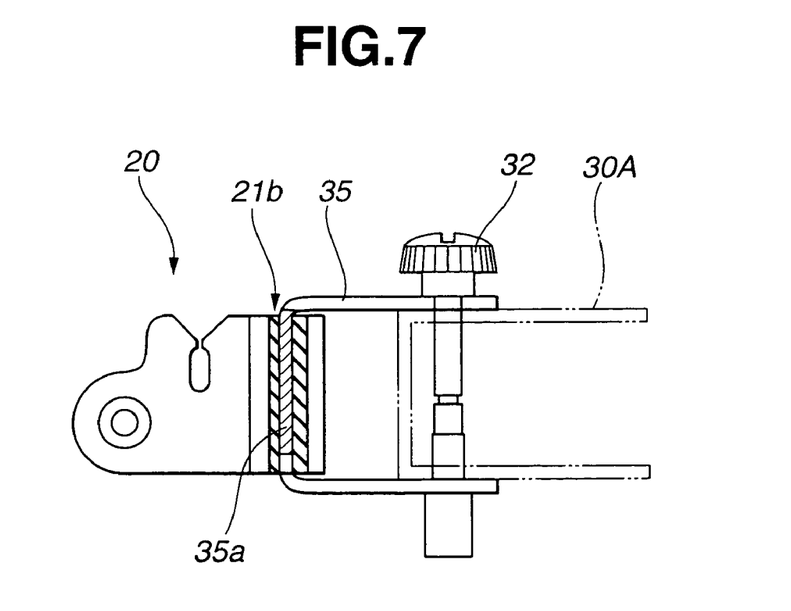
FIG. 7 is a diagram illustrating the holding device mounted on the fixture.

On the other hand, the locking grooves 21b of the fixed portion 21 are fitted to a pair of locking portions 35a formed in a mounting hardware 35 shown in FIG. 6. The mounting hardware 35 is fixed by a fixing screw 32 to the distal portion of, for example, an arm member 30A as shown in FIG. 7 that has a joint portion in an intermediate portion.

The width of each of the locking grooves 21b is formed a little smaller than the thickness of each of the locking portions 35a. Alternatively, the distance between locking portions 35a is made smaller than the wall thickness between the locking grooves 21b. Thereby, the locking grooves 21b is reliably fitted to the mounting hardware 35 under the elastic force of the holding device 20.

The fixing screw 32 is inserted through through-holes 35b formed in the mounting hardware 35.

Operations of the holding device 20 with the above-described features will now be described.

First, the operator inserts the insertion portion 11 of the endoscope 3 through the anus. Then, when attempting to check a bending state of the insertion portion 11, the probe 1 is inserted into the therapeutic device insertion channel 15.

As indicated by the broken lines in FIG. 1, the probe 1 is suspended in advance from the holding device 20. Also, the arm member 30 has been turned with respect to the insertion shape detecting device 7, so that the holding device 20 is disposed close at the operator's hand.

Figure 8:
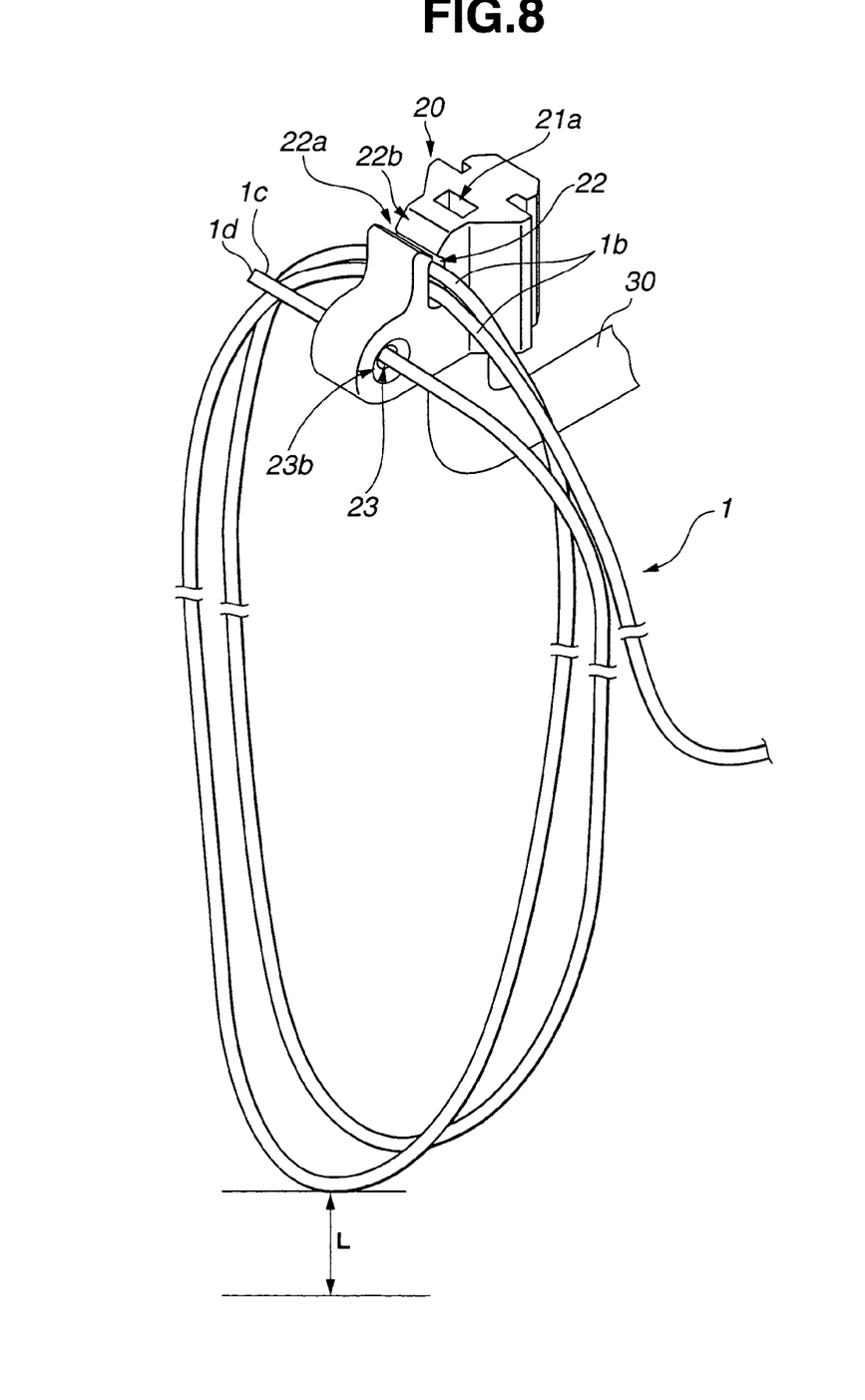
FIG. 8 is a representation of a probe suspended from the holding device.

The probe 1 is now removed from the holding device 20. Specifically, the distal portion 1c of the probe 1 shown in FIG. 8 is first withdrawn from the holding hole 23. Next, the intermediate portion 1b of the probe 1 adjacent to the distal portion thereof is removed from the holding groove 22 through the notch portion 22a, and then the probe 1 is inserted into the therapeutic device insertion channel 15. Then, an insertion portion shape image is displayed on the screen of the second monitor 8. The operator can make a check of the insertion portion shape by observing this insertion portion shape image.

Next, observing an endoscope image displayed on the screen of the first monitor 5, when the operator determines, for example, that it is necessary to collect a tissue biopsy, a grasping forceps (not shown) is inserted into the therapeutic device insertion channel 15.

At this time, for example, while instructing a registered nurse or the like to prepare for a grasping forceps, the operator must withdraw the probe 1 from the therapeutic device insertion channel 15, and in turn, must insert the grasping forceps into the therapeutic device insertion channel 15. Thus, the operator first withdraws the probe 1 from the therapeutic device insertion channel 15.

Here, as shown in FIG. 8, the intermediate portion 1b of the probe 1 adjacent to the proximal portion thereof is placed into the holding groove 22 through the notch portion 22a of the holding device 20 disposed close at the operator's hand.

Next, the probe 1 is withdrawn from the therapeutic device insertion channel 15, and this time, the intermediate portion 1b of the probe 1 adjacent to the central part thereof is placed into the holding groove 22 through the notch portion 22a. After the probe 1 has been completely withdrawn from the therapeutic device insertion channel 15, the distal portion 1c of the probe 1 is inserted through the holding hole 23.

Thereby, the elongated probe 1 can be suspended from the holding device 20 with a plurality of loops each having a relatively large diameter formed. Here, the lowermost end of the probe 1 is held apart from the floor surface of the examination room, e.g., by a distance of L, without contacting the floor surface of the examination room (see also FIG. 1).

In this manner, disposing, close at the operator's hand, the holding device having the holding hole and holding groove formed in a predetermined place, enables a single operator to efficiently withdraw and suspend the elongated probe from the holding device, without allowing the elongated probe to contact the floor surface of the examination room.

Furthermore, providing the predetermined spacing between the holding hole and holding groove prevents a hand from contacting the intermediate portion of the probe when treating the distal portion of the probe.

Moreover, providing the rectangular hole and the pair of locking grooves in the fixed portion allows the fixed portion to adapt to a plurality of types of mounting portions of the arm member.

Figure 9:
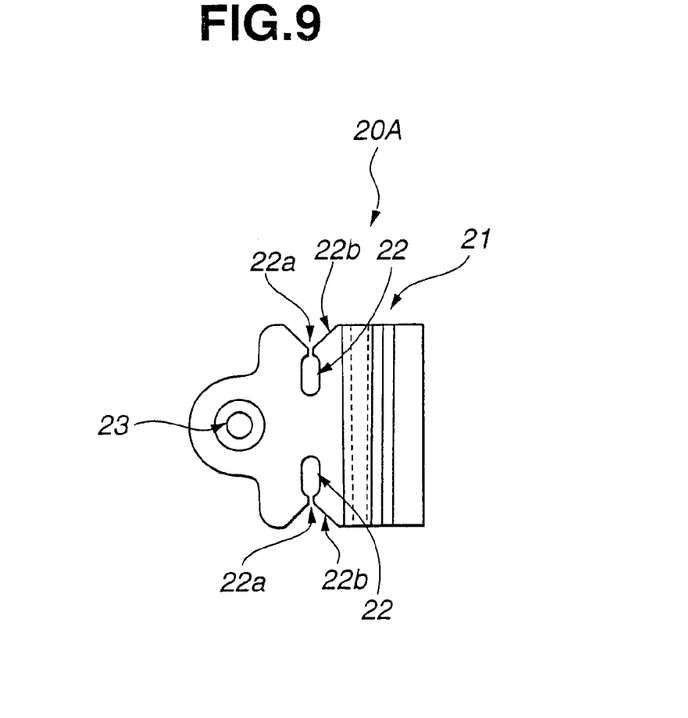
FIG. 9 is a diagram illustrating a holding device having another construction.
Figure 10:
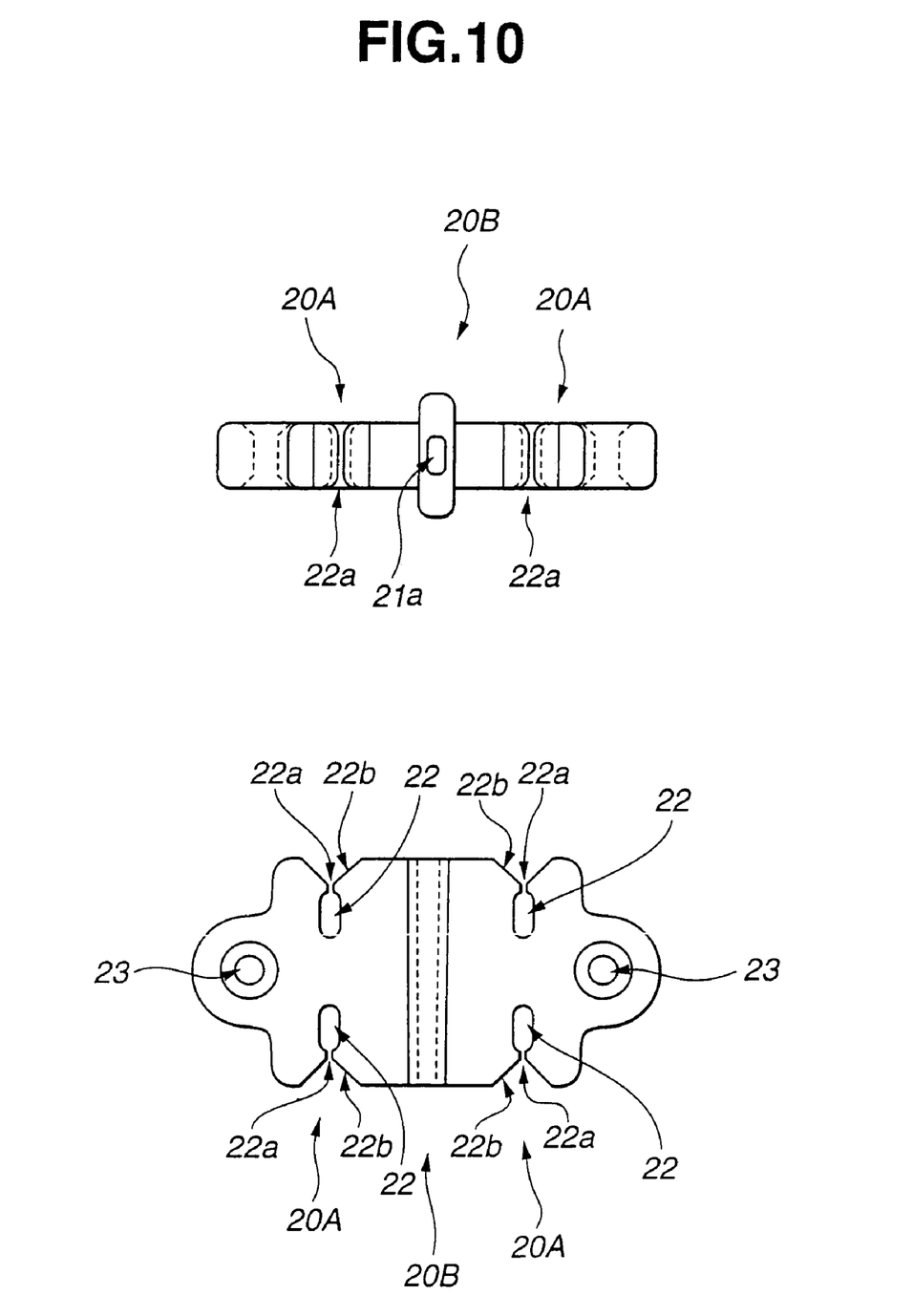
FIG. 10 is a diagram illustrating the top surface and the side surface of a holding device having still another construction.

The shape of the holding device is not limited to the one shown in the above-described embodiment. For example, as shown in FIG. 9, the holding device may be a holding device 20A that has a pair of holding grooves 22 each having a notch 22a. Alternatively, as shown in FIG. 10, the holding device may be a holding device 20B that has the holding devices 20A shown in FIG. 9 on both sides of the rectangular holes 21a.

The holding device according to this embodiment is formed of an elastic material for the purpose of holding the probe. However, when the holding device is to be used for the purpose of holding a therapeutic device such as a grasping forceps, or the like, a material to match the therapeutic device may be selected to thereby form the holding device using the material.

Also, the holding device may be a reuse type that can be reused by disinfecting and sterilizing it after use, or alternatively may be a single-use type that is thrown away after one use.

INDUSTRIAL APPLICABILITY

As described above, the holding device according to the present invention is useful for quickly placing therein the elongated therapeutic device or probe that is to be inserted into or withdrawn from the therapeutic insertion channel of the endoscope, without allowing the therapeutic device or prove or the like to temporarily contact a floor surface.

The invention claimed is:
1. A holding device comprising:
   a fixed portion removable with respect to a predetermined member;
   a holding groove formed further toward a front side than the fixed portion and having a notch portion with a predetermined width, the notch portion being passed through by an intermediate portion of a therapeutic device or probe; and
   a holding hole into which a distal portion of the therapeutic device or the probe is placed, the holding hole having a predetermined diameter and being formed further toward the front side than the holding groove.
2. The holding device according to claim 1, wherein the depth of the holding groove is formed to a sufficient extent to allow the intermediate portion of the therapeutic device or probe to be pressed down into the holding groove at least twice.
3. The holding device according to claim 1, wherein a predetermined spacing is provided between the bottom portion of the holding groove and the top portion of the holding hole.
4. The holding device according to claim 1, wherein the fixed portion has at least a rectangular hole or locking grooves.

* * * * *